United States Patent [19]

Zanno et al.

[11] Patent Number: 4,534,988
[45] Date of Patent: Aug. 13, 1985

[54] FLAVORING WITH 1, 3-OXATHIANES

[75] Inventors: Paul R. Zanno, Hopewell Junction; Thomas H. Parliment, New City, both of N.Y.

[73] Assignee: General Foods Corporation, White Plains, N.Y.

[21] Appl. No.: 176,947

[22] Filed: Aug. 11, 1980

[51] Int. Cl.³ .............................................. A23L 1/231
[52] U.S. Cl. ...................................... 426/535; 549/14
[58] Field of Search .................. 426/535, 533; 549/14

[56] References Cited

U.S. PATENT DOCUMENTS

| 3,900,498 | 8/1975 | Dubs et al. | 426/535 X |
| 4,031,257 | 6/1977 | Wilson et al. | 426/535 |
| 4,042,601 | 8/1977 | Wilson et al. | 549/14 |
| 4,220,561 | 9/1980 | Winter | 426/535 X |
| 4,262,030 | 4/1981 | Winter | 426/535 |

OTHER PUBLICATIONS

Badings et al., Formation of Odorous Compounds from Hydrogen Sulphide and 2-Butenal, 161, Z. Lebens Unter-Forsch., 53–59, (1976).
Kleipool et al., Reaction of Hydrogen Sulphide with 2-Alkenals, 161, Z. Lebens Unter-Forsch, 231–238, (1976).

*Primary Examiner*—Joseph Golian
*Attorney, Agent, or Firm*—Richard D. Schmidt; Thomas Savoie; Daniel J. Donovan

[57] ABSTRACT

This invention relates to 1, 3-oxathianes, their preparation and their use as food flavoring materials. The preferred embodiments have flavors reminiscent of meats, especially chicken or beef. These oxathianes have the general formula:

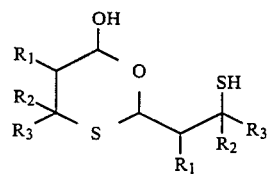

wherein $R_1$, $R_2$ and $R_3$ are the same or different radicals and which are H or $C_1$ to $C_3$ alkyl.

4 Claims, No Drawings

FLAVORING WITH 1, 3-OXATHIANES

DESCRIPTION

1. Technical Field

This invention relates to food and beverage flavorants. More particularly, it relates to synthetic flavorants useful in imparting beef or chicken organoleptic qualities to food products. This invention especially relates to particular 1,3-oxathianes and their use as food flavorants.

2. Background of Prior Art

Flavor has been defined as the blend of taste and smell sensations evoked by a substance in the mouth. Flavor is also described as that property of a food or a substance used in food that causes a simultaneous reaction or sensation of taste on the tongue and odor in the olfactory center in the nose. These definitions include two phenomena, taste and smell, as part of the sensation known as taste. It has been suggested the vision, hearing and tactile sense also contribute to the total impression of flavor.

Food finds general acceptance when four quality factors are in proper qualitative proportion. These factors are appearance, mouthfeel, flavor and nutritive value. Since flavor is an important factor in food acceptance, the increased use of prepared foods has caused an expanded use of flavorants. This has resulted in more research and development in flavorants and their use.

Flavoring materials are added to prepared foods by food processors to provide a desired flavor or to enhance the flavor of the processed food product. These flavoring materials may be described as natural or artificial. Natural flavorants include such materials as spices and herbs; essential oils and their extracts, concentrates and isolates; fruit and fruit juices; animal and vegetable materials and their extracts; and aromatic chemicals isolated from natural products. Artifical flavorants are chemical compounds such as aliphatic, aromatic and terpene compounds which are made synthetically as opposed to those flavorants isolated from natural sources.

The increasing use of artificial flavorants has led to the availability of artificial flavor materials which permit a close approach to natural flavors. There appears to be little, if any, difference in safety or nutritional value between a naturally occurring flavor and its synthetic substitute. Thus an artificial flavor is no less safe, no less nutritious and is not inherently less desirable than a natural flavor. The sole distinguishing point appears to be economic—in most instances, natural flavor is more expensive than the artificial flavor.

Synthetic flavors in common use today include: Benzyl acetate (fruity raspberry and cherry), methyl salicylate (winter-green), furfuryl mercaptan (coffee), diacetyl (butter), methyl-5-(B-hydroxyethyl)thiazole (meat) and 2,6-dimethoxyphenol (smoke).

U.S. Pat. No. 3,900,498 of Dubs et al relates to 2-thietanols, which have particular flavor properties partly reminiscent of fried eggs and meat and partly reminiscent of onions. The patentees prepared these 2-thietanols by reacting 2-alkenals with hydrogen sulfide in an aprotic solvent in which hydrogen sulfide is soluble and in the presence of an organic base catalyst. The reaction was performed by saturating the solvent with $H_2S$ at low temperature ($-10°$ C.), adding an amine catalyst and then making additions of 2-alkenal over a 2 hour period while $H_2S$ was continuously being introduced. The mixture was stirred for an additional 2 hours at $-10°$ C. then permitted to stand for 12 hours at $-28°$ C. and acidified. The organic phase was separated, acid washed, water washed, dried and vacuum distilled to yield the desired 2-thietanol.

Badings, Kleipool and their co-workers studied the reaction of 2-alkenals with $H_2S$ in aprotic solvents and in dilute aqueous solutions at different pH levels. They found that strong odorous products were formed when $H_2S$ reacted with 2-butenal under different conditions. In aprotic solvents following the procedure of Dubs et al and in natural aqueous solutions, they obtained 3-mercaptbutanal which dimerized on standing to a 1,3-oxathiane. They did not detect the 2-thietanol of Dubs et al although a variety of other reaction product were obtained if a higher boiling fracion from the reaction product was heated. In acidic aqueous solutions Kleipool, Badings et al identified a 1,3-dithiin as the main component of the reaction products. In all some 10–11 products were identified and subjected to organoleptic evaluations. In acidic solution, the reaction mixture smelled like onion and leek but in neutral solution an omelette odor dominated. The dimer was not identified organoleptically and no organoleptic evaluations were reported for the aprotic solvent reaction mixtures. Badings et al, "Formation of Odorous Compounds from Hydrogen Sulfide and 2-Butenal," 161 *Z. Lebens. Unter.-Forsch.* 53 (1976), Kleipool et al, "Reaction of Hydrogen Sulfid with 2-Alkenals," ibid. at 231.

It is an object of this invention to provide artificial flavorants useful in providing food products with desirable flavors.

It is another object of this invention to utilize 2-alkenal reaction products as artificial flavorants.

It is still another object of this invention to prepare artificial flavorants having beef or chicken flavors for use in preparing food products.

DISCLOSURE OF THE INVENTION

In accordance with the present invention it has been found that 1,3-oxathianes can be prepared in either a solvent system or a solventless system. These products provide very distinct flavors of beef or chicken. When added to foods, these flavors impart prominent beef and chicken flavors and flavor notes.

The solvent system is directed to a method of preparing a 1,3-oxathiane which comprises:

(a) dissolving in an aprotic solvent an aldehyde having the formula:

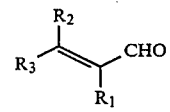

wherein $R_1$, $R_2$ and $R_3$ are the same or different radicals and which are H or $C_1$ to $C_3$ alkyl;

(b) contacting the solution of step (a) with gaseous hydrogen sulfide for from 0.5 to less than 2.0 hours and at a temperature of 0° to 25° C. whereby a 1,3-oxathiane having the formula:

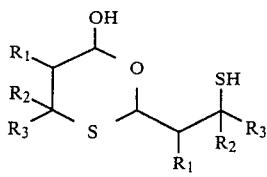

is formed, and (c) recovering said 1,3-oxathiane from the reaction mixture of step 1(b) as the product therefrom.

The solventless system is directed to a method of preparing a 1,3-oxathiane which comprises:

(a) contacting an aldehyde, having the formula:

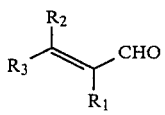

wherein $R_1$, $R_2$ and $R_3$ are the same or different radicals and which are H or $C_1$ to $C_3$ alkyl,
with liquid hydrogen sulfide in the presence of an anion exchange resin for a time sufficient to effect a reaction whereby a 1,3-oxathiane having the formula:

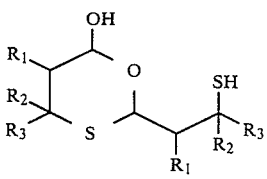

is formed, and (b) recovering said 1,3-oxathiane from the reaction mixture of step (a) as the product therefrom.

This invention is also directed to the 1,3-oxathianes prepared by either the above described solvent process or the above described solventless process.

Further the invention is a method of imparting an organoleptic quality to an edible substrate which comprises:

(a) admixing with an edible substrate an organoleptically effective amount of an organic compound having the formula:

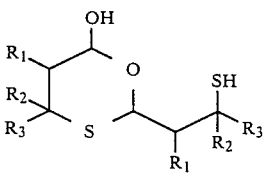

wherein $R_1$, $R_2$ and $R_3$ are the same or different radicals and which are H or $C_1$ to $C_3$ alkyl.

BEST MODE FOR CARRYING OUT THE INVENTION

Briefly this invention relates to 1,3-oxathianes, their preparation and their use as food flavoring materials. These oxathianes have the formula:

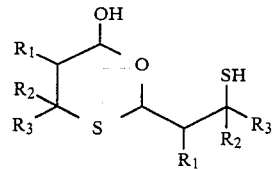

wherein $R_1$, $R_2$ and $R_3$ are the same or different radicals and which are H or $C_1$ to $C_3$ alkyl. As such, $R_1$, $R_2$ and $R_3$ may all be H or one R may be H and the other two R's may be the same or different $C_1$ to $C_3$ alkyls or two R's may be H and the other R may be a $C_1$ to $C_3$ alkyl. It is within the scope of this invention that the R's be methyl, ethyl, normal-propyl and iso-propyl. It is not contemplated that when two R's are $C_1$ to $C_3$ alkyls that they be required to be different.

When small quantities of the oxathianes of this invention are added to foodstuffs they impart very distinctive flavors thereto. The preferred embodiments have flavors reminiscent of meats, especially chicken or beef, and thus are especially useful in the manufacture of preparation of food stuffs wherein such flavors are desirable. One skilled in the art will readily appreciate that these flavors may find use in such foodstuffs as soups, soup concentrates, meat and chicken analogs, wet and dry mixes for stuffings and coatings, gravies, pet foods that are considered dry, soft moist and canned, as well as in combination with other flavors or flavor notes for new flavorants.

The 1,3-oxathianes of this invention may be added to foodstuffs as such or combined with diluents or carriers known in the flavor art so as to simplify the addition of the desired small quantity of the flavorant in the form of a liquid or a powder. The amount of the flavorant to be added will depend, of course, on the level and intensity of the flavor desired and the particular flavor of the 1,3-oxathiane being employed as well as the individual preference of the consumer. Thus, concentration levels can vary from 0.1 to 100,000 parts per billion in foodstuffs, with levels of 10 to 1,000 ppb usually providing the desired flavor intensity. Most preferred levels are 50 to 600 ppb.

Since obtention of the beefy or chickeny flavors do not require any type of interaction between the components of the flavor composition or fixation of each to the other, the desirable flavor may be obtained by adding the components concurrently or sequentially to the particular food or beverage system. When the components of this invention are to be utilized in dry form for incorporation into dry solid systems or where fixation of these components is generally desired, this may be accomplished by any method known in the art to effect the desired result without at the same time causing degradation of either component. Exemplary of such methods would include fixation by co-drying the flavor components on soluble, bland polysaccharides such as polyglucose, polymaltose, polymaltodextrins or the like, dextrins having D.E. of less than about 20 and starch hydrolysates to mention a few. Other known fixatives such as gums, for example, gum arabic, gum ghatti, xanthan gum, carboxymethyl cellulose, and the like are also appropriate. Spray drying and drum drying tend to lessen the activity of said constituents due to the slight oxidation and volatilization that takes place during these processes. However, spray drying may be employed where slight loss is of little concern, but drum drying should not be used due to the excessive heat involved unless the drum drying facility limits the amount of heat energy input to a point whereat a drum temperature not appreciably in excess of 180° F. is utilized. Freeze drying provides another method known in the art to fix the 1,3-oxathaines. Freeze drying offers the advantage of having an absence of heat. As such, the freeze drying could be considered a method to stabilize the 1,3-oxathianes.

The 1,3-oxathianes of this invention are prepared by reacting hydrogen sulfide with an unsaturated aldehyde. The reaction is conducted in either a solvent or a solventless system. The unsaturated aldehyde has the formula:

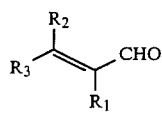

where $R_1$, $R_2$ and $R_3$ are the same or different and are H or $C_1$ to $C_3$ alkyl. Typical aldehydes employed include propenal(acrolein), 2-butenal(crotonaldehyde), trans 2-methyl-2-butenal(tiglicaldehyde) and cis 2-methyl-2-butenal.

In the solvent system, the aldehyde is dissolved in an aprotic solvent, such as chloroform or methylene dichloride. Other appropriate aprotic solvents may be employed also. The reaction may be conducted without a catalyst but the use of a basic organic catalyst is preferred. Such catalysts as ammonia, triethylamine, tetramethylammonium hydroxide and the like may be employed. The reaction is typically conducted at about room temperature or below so temperatures of $-5°$ to 30° C., preferably 0° to 25° C., are employed. Pressure is not critical in this reaction so atmospheric or other appropriate pressure may be employed.

By combining the catalyst with the solution of aldehyde and solvent, the desired products are formed in a short period of time when hydrogen sulfide is bubbled into the liquid mixture. Reaction times of 0.5 to less than about 2 hours are satisfactory. Although a longer time, i.e. 2 hours and above, may be employed, side reactions often develop at these longer times resulting in products other than the desired 1,3-oxathianes which complicates the recovery and purification process and reduces the yield. It has been found, therefore, that 0.5 to less than 2 hours should be employed in this solvent system.

The 1,3-oxathianes may be recovered from the reaction mixture by known techniques, such as vacuum distillation.

The solventless system is conducted with the hydrogen sulfide in liquid form. Since hydrogen sulfide has a boiling point of appriximately $-59.6°$ C. this requires temperatures below this level where atmospheric pressure is employed. Higher temperatures may be employed but this, of course, requires the use of superatmospheric pressures. Those skilled in the art will appreciate the operating conditions necessary to maintain the hydrogen sulfide in a liquid condition during the reaction. This solventless reaction is conducted in the presence of an anion exchange resin, especially a strong anion exchange resin. Ion exchange resins are usually based on cross-linked polystyrene and may be obtained as either cation-exchange resins or anion exchange resins. The anionic resins may contain either quaternary ammonium groups which makes them strongly basic or other amino groups which renders them weakly basic. The quaternary ammonium groups are typically trimethyl benzyl ammonium or dimethyl hydroxyethyl benzyl ammonium. Among the useful strongly basic anion exchange resins which may be employed are those supplied by Rohm and Haas Company under the trade name Amberlite. Amberlite IRA-400 is an especially preferred resin. Reaction times are not critical and will be dependant on the operating temperature and pressures employed. As in the the solvent system, the 1,3-oxathianes are recovered from the reaction mixture by known means, such as vacuum distillation.

Among the 1,3-oxathianes which may be prepared by the above procedure, it has been found that certain of these provide very distinct and desirable flavors which makes them particularly useful as an artificial flavorant for food. Where $R_1$, $R_2$ and $R_3$ are each hydrogen, the product, 2-(2'mercaptoethyl)-4-hydroxyl-1,3-oxathiane, provides a charred fat, roasted, beefy flavor. Where $R_1$ and $R_2$ are each hydrogen and $R_3$ is methyl, the product, 2-(2'mercaptopropyl)-4-hydroxy-6-dimethyl-1,3-oxathiane, has a roasted beef, charred beef fat flavor. Where $R_1$ and $R_3$ are each methyl and $R_2$ is hydrogen, the product 2-(1'methyl-2'mercaptopropyl)-4-hydroxy-5,6-dimethyl-1,3-oxathiane has a brothy, chickeny, chicken soup flavor. The following examples will serve to illustrate the subject invention.

EXAMPLE I

One (1) milliliter (ml.) of 2-butenal(crotonaldehyde) was added to 20 ml. of chloroform. Ammonia and hydrogen sulfide were bubbled simultaneously into this solution under room temperature conditions for 30 minutes. A clear, viscous liquid product recovered from the reaction mixture by vacuum distillation had an impressive roasted beef, charred beef, meaty character. This product was subjected to infrared and mass spectroscopic analysis and identified as 2-(2'mercaptopropyl)-4-hydroxy-6-methyl-1,3-oxathiane which has the structure:

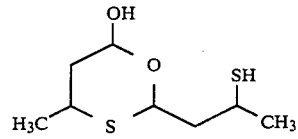

The IR spectrum (neat) showed bands at: 3400, 2960, 2920, 2550, 1450, 1375, 1270, 1195, 1040, 970, 890 and 770 cm$-1$. The band at 2550-cm$-1$ indicates the mercapto group. The mass spectra of the six most intense ions was: 104 (100%), 61 (88%), 71 (74%), 42 (64%), 208 (47%). Mass spectral peak matching was done by comparison to known fragment ions of perfluorokerosene (PFK). The following is the result of those measurements.

| NOMINAL ION | HIGH RESOL. MEASUREMENT | ACTUAL VALUES |
|---|---|---|
| 208 | 208.0576 | 208.0592 = $C_8H_{16}O_2S_2$ |
| 104 | 104.0295 | 104.0296 = $C_4H_8OS$ |
| 86 | 86.0231 | 86.0190 = $C_4H_6S$ |
| 71 | 71.0513 | 71.0497 = $C_4H_7O$ |

The empirical data for molecular and fragment ions are consistent with the above structural formula.

Although the same solvent and the reactants were employed in Example 1 of U.S. Pat. No. 3,900,498, the product obtained there was a 2-thietanol as shown by the IR spectrum which showed no mercapto band at 2550 cm−1. Further evidence of a different product is the fact that this 2-thietanol had an egg-like sulfurous odor and egg-like flavor while the 1,3-oxathiane of the above example had a beefy character.

EXAMPLE II

The 1,3-oxathianes of this invention may be prepared by a solventless method:

A three-necked 100 ml. round bottom flask was fitted with a gas inlet tube, drying tube and dry ice-acetone condenser. To this flask was added 20 ml of crotonaldehyde and 5 grams of Amerlite IRA-400 (trade name for a strong anion exchange resin). Hydrogen sulfide gas was condensed into the cooled flask until the volume increased by 20 ml. The cooled mixture was then directly transferred to a pre-cooled (−78° C.) Paar Bomb apparatus and sealed. The vessel was allowed to reach room temperature (23° C., 100 psi) and then heated to 60° C. in an oven for 4 hours (pressure reaching 400 psi). After cooling, the contents were removed, filtered to separate the anion exchange resin and distilled under vacuum. Distillation yielded 12 gms. of a clear, viscous liquid identified as 2-(2′mercaptopropyl)-4-hydroxy-6-methyl-1,3-oxathiane by the infrared and mass spectroscopic analysis of Example I. This product had the same beefy character as the product prepared by the aprotic solvent method of Example. I.

EXAMPLE III 0.5 ml of triethyl amine and 5 ml of trans 2-methyl-2-butenal(tiglicaldehyde) were added to 20 ml of methylene chloride. Hydrogen sulfide was bubbled into this solution for about two hours. A clear, viscous liquid recovered from the reaction mixture had a brothy, chickeny, chicken soup character. This product was subjected to infrared and mass spectroscopic analysis and identified as 2-(1′methyl-2′-mercaptopropyl)-4-hydroxy-5,6-dimethyl-1,3-oxathiane which has the structure:

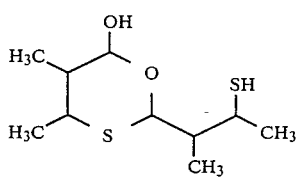

The IR spectrum (neat) showed bands at: 3400, 2960, 2920, 2550, 1450, 1375, 1020, 890 and 770 cm−1. The band at 2550 cm−1 indicates the mercapto group. The mass spectra of the six most intense ions was 85 (100%), 56 (86%), 61 (82%), 118 (62%), 236 (45%), 55 (38%). Mass spectral peak matching was done by comparison to known fragment ions of perfluorkerosene (PFK). The following is the result of those measurements:

| NOMINAL ION | HIGH RESOL. MEASUREMENT | ACTUAL VALUES |
|---|---|---|
| 236 | 236.0974 | 236.0905 = $C_{10}H_{20}O_2S_2$ |
| 118 | 118.0426 | 118.0453 = $C_5H_{10}OS$ |
| 85 | 85.0694 | 85.0653 = $C_5H_9O$ |

The empirical data for molecular and fragment ions are consistent with the above structural formula.

EXAMPLE IV 1 ml of propenal(acrolein) was added to 20 ml of chloroform at 0° C. Ammonia and hydrogen sulfide were bubbled simultaneously into this solution maintained at 0° C. for 30 minutes. A clear viscous liquid recovered from the reacton mixture by vacuum distillation had a very impressive roasted, charred adipose, beefy, crispy meat character. This product was identified by infrared and mass spectroscopic analysis as 2-(2′-mercaptoethyl)-4-hydroxy-1,3-oxathiane which has the structure:

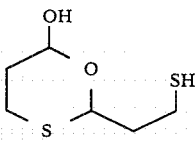

EXAMPLE V

Various amounts of the 1,3-oxathiane of Example 1 and 2 were evaluated as flavorants in various carriers and foodstuffs to determine concentration levels to obtain desirable flavor levels in each of the materials tested. The most favorable concentration levels for these two 1,3-oxathianes are summarized in the tables below:

| | ppb |
|---|---|
| Spring water (threshold level) | 10 |
| Beef gravy enhancement | 200 |
| Beef soup mix | 300 |
| Spring water (threshold level) | 0.5 |
| Dry chicken soup mix | 70 |
| Chicken gravy enhancement | 70 |
| Chicken stuffing mix | 140 |

The above examples and explanations are for the purpose of teaching those skilled in the art how to practice the invention. Upon reading the above disclosure, those skilled in the art will be aware of a number of modifications and variations. It is contemplated that these modifications and variations be included within the scope of the present invention which is defined by the following claims.

What is claimed:

1. A foodstuff having added thereto, as an active flavoring ingredient from 0.1 to 100,000 parts per billion, and effective to impart a beef or chicken flavor thereto, of a compound selected from the formula:

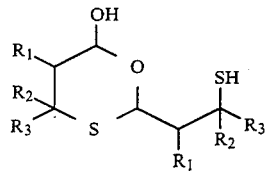

Wherein $R_1$, $R_2$ and $R_3$ are the same or different radicals and which are H or $C_1$ to $C_3$ alkyl.

2. A foodstuff according to claim 1 wherein the flavoring ingredient compound comprises $R_1$ and $R_2$ are H and $R_3$ is $CH_3$ whereby the organoleptic quality is a roasted beef, charred beef fat, meaty flavor.

3. A foodstuff according to claim 1 wherein the flavoring ingredient compound comprises $R_1$, $R_2$ and $R_3$ are each H, whereby the organoleptic quality is a roasted, charred adipose, beefy, crispy meat flavor.

4. A foodstuff according to claim 1 wherein the flavoring ingredient compound comprises $R_1$ and $R_3$ are each $CH_3$, and $R_2$ is H, whereby the organoleptic quality is a brothy, chickeny, chicken soup flavor.

* * * * *